United States Patent [19]
Butterfield

[11] Patent Number: 5,827,223
[45] Date of Patent: Oct. 27, 1998

[54] UPSTREAM OCCULSION DETECTION SYSTEM

[75] Inventor: Robert D. Butterfield, Poway, Calif.

[73] Assignee: Alaris Medical Systems, Inc., San Diego, Calif.

[21] Appl. No.: 522,001

[22] Filed: Aug. 31, 1995

[51] Int. Cl.$^6$ .................................................. A61M 31/00
[52] U.S. Cl. ................................................................ 604/65
[58] Field of Search ................................ 604/65, 49–53, 604/66, 67, 30–34; 128/DIG. 12, DIG. 13

[56] References Cited

U.S. PATENT DOCUMENTS

| | | | |
|---|---|---|---|
| 4,277,226 | 7/1981 | Archibald | 417/38 |
| 4,460,355 | 7/1984 | Layman | 604/118 |
| 4,530,696 | 7/1985 | Bisera et al. | 604/253 |
| 4,534,756 | 8/1985 | Nelson | 604/50 |
| 4,617,014 | 10/1986 | Cannon et al. | 604/67 |
| 4,710,163 | 12/1987 | Butterfield | 604/65 |
| 4,731,057 | 3/1988 | Tanaka et al. | 604/153 |
| 4,743,228 | 5/1988 | Butterfield | 604/50 |
| 4,836,752 | 6/1989 | Burkett | 417/12 |
| 4,846,792 | 7/1989 | Bobo, Jr. et al. | 604/50 |
| 4,898,576 | 2/1990 | Philip | 604/50 |
| 4,959,050 | 9/1990 | Bobo, Jr. | 604/49 |
| 5,078,682 | 1/1992 | Miki et al. | 604/65 |
| 5,087,245 | 2/1992 | Doan | 604/67 |
| 5,096,385 | 3/1992 | Georgi et al. | 417/18 |
| 5,098,380 | 3/1992 | Aizawa et al. | 604/67 |
| 5,103,211 | 4/1992 | Daoud et al. | 340/608 |
| 5,116,203 | 5/1992 | Natwick et al. | 417/53 |
| 5,356,378 | 10/1994 | Doan | 604/65 |
| 5,423,743 | 6/1995 | Butterfield | 604/50 |

FOREIGN PATENT DOCUMENTS

| | | | |
|---|---|---|---|
| 0 431 310 A1 | 6/1991 | European Pat. Off. | A61M 5/168 |
| 0 554 716 A1 | 11/1993 | European Pat. Off. | A61M 5/142 |

*Primary Examiner*—Michael Buiz
*Assistant Examiner*—Manuel Mendez
*Attorney, Agent, or Firm*—Fulwider Patton Lee & Utecht, LLP

[57] ABSTRACT

A pumping segment of a fluid line alternately in fluid communication with the upstream and downstream portions of the fluid line connects a fluid supply to a fluid receiver. A pressure sensor located downstream of the segment monitors the pressure during the segment's communication with the upstream and downstream ends. The pressure difference is used to establish a pressure threshold against which the average pressure is compared to determine if an upstream occlusion exists. Should the average pressure fall within a cautionary zone, the pump is reversed to examine the pressure difference once again. Based on the pressure difference during the reversal, a pressure threshold line may be adjusted thereby adapting to fluid administration conditions.

12 Claims, 9 Drawing Sheets

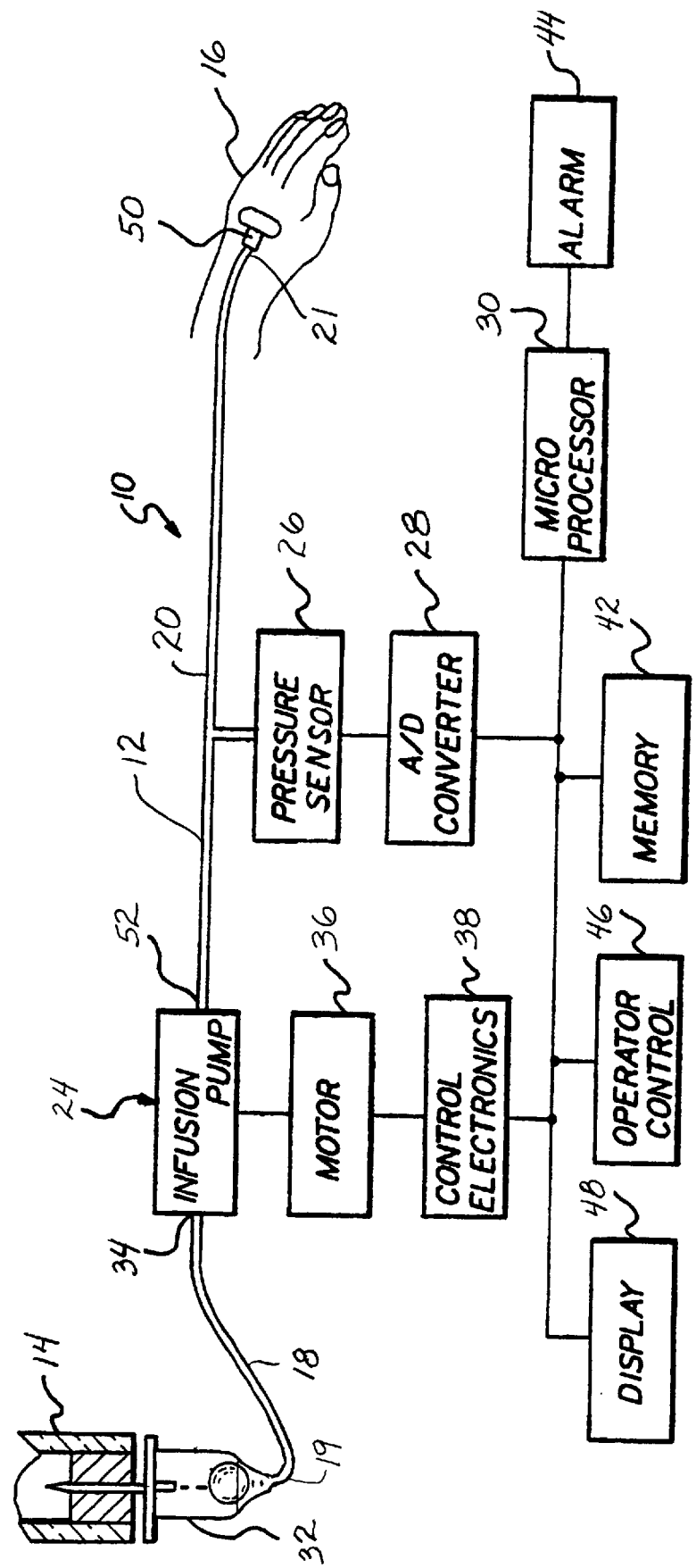

UPSTREAM OCCULSION DETECTION SYSTEM

BACKGROUND

1. Field of the Invention

The invention relates generally to monitoring fluid flow, and more particularly, to detecting upstream fluid conditions in an intravenous fluid administration system.

2. Description of Related Art

Fluid delivery systems for infusing parenteral fluids are commonly used in hospitals and typically include an inverted bottle or bag or other means of supply of parenteral fluid, an intravenous (IV) administration set that is secured to the supply of parenteral fluid and includes a flexible IV tube, a cannula that is mounted to the distal end of the flexible IV tube and that is adapted to be inserted into the patient's blood vessel to thereby infuse the parenteral fluid, and an infusion pump. Such infusion pumps provide a positive means for controlling the amount of fluid administered, and are an alternative to gravitational flow systems. In many cases, the pump is a peristaltic type in which a plurality of fingers, rollers, or other devices sequentially constrict along a moving zone of occlusion the flexible IV tube through which the parenteral fluid is supplied.

A common problem facing infusion systems is the evaluation of the condition of the fluid supply system upstream of the pump. For example, where an occlusion of the tube exists upstream of the pump, the pump will not succeed in infusing the parenteral fluid to the patient even though the pump may continue to operate. Similarly, where the parenteral fluid supply becomes depleted, once again the pump may continue to operate but no parenteral fluid will be delivered to the patient.

A prior method for detecting depletion of the fluid supply or an upstream occlusion was visual observation. A drip chamber may be inserted in the fluid line at a position downstream from the fluid supply for monitoring the rate and quantity of fluid administered. However, visually verifying the existence of drops requires the time of an attendant which can be an undesirable burden on the hospital staff.

In infusion systems utilizing peristaltic pumps, detection of upstream occlusions has been accomplished through the use of an opto-electric drop detector combined with a drip chamber. The drop detector automatically detects upstream occlusions, such as occlusions caused by a clamp or kink in the upstream tubing, by detecting an absence of drops. However, movement of the IV administration set, if severe enough, can cause extra drops to fall from the drop former or can interrupt the drops, causing false counts and false alarms. Ambient light can also interfere with an optical drop sensor and render it less accurate.

Another method of detecting upstream occlusions involves the addition of a pressure sensor to the fluid line upstream of the pump. However, the use of these devices can add considerable cost to both the instrument and the disposable portion of the IV administration set.

Another method for detecting upstream occlusions is to incorporate a pressure sensor into the pumping mechanism of the infusion pump itself. In one such device, a pressure transducer is placed in the middle of the pumping area, allowing direct measurement of the pressure in the pump tubing segment, which is indicative of the inlet pressure. However, this can adversely affect flow uniformity and may require substantial modifications to the pumping mechanism.

Pump systems have been disclosed that include a downstream pressure sensor used for detecting improper fluid communication with the patient. Such systems include U.S. Pat. No. 4,743,228 to Butterfield; U.S. Pat. No. 4,460,355 to Layman; U.S. Pat. No. 4,534,756 to Nelson; and U.S. Pat. No. 5,356,378 to Doan In operation, peristaltic pump mechanisms sequentially occlude the pumping segment of the tube, also known as the pumping control segment, to alternately expose the pumping segment to fluid communication with the upstream and downstream portions of the fluid line. The pumping segment is at upstream pressure when exposed to the upstream portion of the fluid line. When the pumping segment is subsequently exposed to the downstream portion, the fluid within the pumping segment, which was at upstream pressure, causes a change in pressure, i.e., a pressure difference, as the pumping segment pressure equalizes with the downstream portion.

Some pump systems using downstream pressure sensors have utilized analysis of such pressure differences to detect upstream occlusions. If a large negative pressure difference occurs, an upstream occlusion is presumed. However, pumping into high downstream pressures can create pressure waveform conditions, including drops in pressure, that mimic the appearance of true upstream occlusions. Additionally, pressure sensors may exhibit substantial offset errors that can also mimic upstream occlusion conditions. Pressure sensors used with IV systems may themselves cause some variance and their readings can vary substantially. Such variances, which may be produced by temperature differences or other factors, can cause false alarms. In some cases, variances can be reduced through compensation circuits or closer tolerances on various mechanical and circuit elements. However, this approach can add substantial expense.

Utilizing an existing downstream pressure sensor to determine upstream fluid conditions can result in less expense both in the pump itself as well as in the entire IV administration set. However, false alarms can erode the usefulness of an occlusion detection system. Accordingly, it is desirable to use a single downstream pressure sensor having less stringent accuracy requirements while avoiding false alarms.

Hence, those skilled in the art have recognized the need for a fluid line monitoring system that can automatically detect upstream fluid line occlusions while minimizing false alarms. Additionally, those skilled in the art have recognized a need to reduce the cost of a system capable of determining such upstream fluid line conditions. The present invention fulfills these needs and others.

SUMMARY OF THE INVENTION

Briefly and in general terms, the present invention provides a system and a method for detecting a condition in an upstream portion of a fluid line coupled between a fluid supply at its upstream (i.e., intake) end and a fluid receiver at its downstream (i.e., outlet) end, comprising a flow control device coupled to a fluid line segment of the fluid line between the upstream and downstream ends for alternately opening the fluid line segment to fluid communication with the upstream end and the downstream end of the fluid line. A pressure sensor senses pressure in the fluid line and provides a pressure signal in response to said pressure sensing. A processor monitors the pressure signal to determine the pressure difference occurring when the fluid line segment is exposed to the pressure from one end of the fluid line after having been exposed to the pressure at the other end of the fluid line. The processor averages the pressure signal, and based on the pressure difference and the pressure average, the processor provides a condition signal indicating a fluid line condition in said upstream portion of the fluid line.

The fluid pressure difference is the temporary change in downstream pressure that occurs at the time when the pumping control segment having fluid at the head (i.e., intake or upstream) pressure is opened to fluid communication with the downstream end of the fluid line. When an upstream occlusion ("USO") occurs, the upstream pressure typically becomes quite low and may form a partial vacuum. When the pumping control segment at low upstream pressure is placed in fluid communication with the downstream portion at higher pressure, fluid rushes from the downstream portion into the pumping control segment, thus causing a temporary pressure drop in the downstream pressure. The magnitude of this pressure drop is the downstream pressure difference.

The current invention discriminates false upstream occlusion indicators by comparing the average pressure to a threshold pressure, with the threshold pressure being a variable determined from the pressure difference.

The invention monitors the downstream pressure over a period of time, such as a single revolution of the peristaltic pump mechanism, to determine an average downstream pressure. The system uses the pressure difference to determine a threshold pressure value. The system compares the average pressure to the threshold pressure to detect an upstream occlusion. In a further aspect, the system activates an occlusion alarm if one or more sequential revolutions of the pump mechanism result in average pressures that exceed threshold pressures.

In a further aspect of the invention, the pressure difference is used to determine two threshold pressures: a first or primary threshold pressure and a second or cautionary threshold pressure. If the average downstream pressure is greater than either of the two threshold pressures, no occlusion is indicated. Where the average pressure is less than the primary threshold pressure, an upstream occlusion is indicated. The second or cautionary threshold pressure, which is typically larger than the primary, is used to indicate a potential upstream occlusion.

If the average pressure is less than the cautionary threshold pressure but greater than the primary threshold pressure, the system presumes that the presence or absence of an upstream occlusion is indeterminate. In such a situation, the system initiates a confirmation test to determine the presence or absence of an upstream occlusion. Such a test typically involves a temporary reversal of the pumping mechanism for a specific portion of the mechanism's rotational cycle. For each temporary reversal, the new pressure difference is monitored and compared against a post-reversal cutoff. Depending on the comparison of the pressure difference obtained after the reversal to the cutoff, the system may adjust the cautionary pressure threshold thereby adapting the system to lessen the chances of false alarms.

Other aspects and advantages of the invention will become apparent from the following detailed description and accompanying drawings, illustrating by way of example the features of the invention.

BRIEF DESCRIPTION OF THE DRAWINGS

FIG. 1 is a block diagram of a system for detecting upstream occlusions in a fluid line incorporating the principles of the invention as applied to an intravascular fluid infusion system;

DETAILED DESCRIPTION OF THE PREFERRED EMBODIMENTS

Figure 2A:
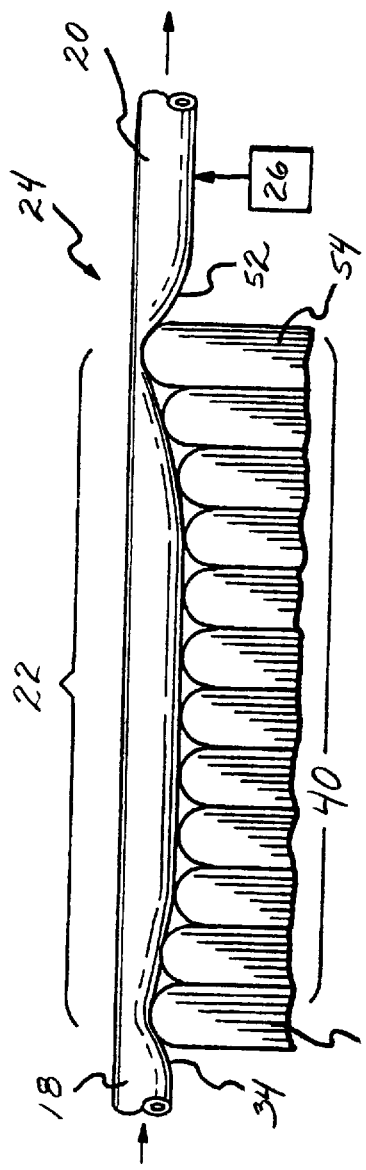
FIGS. 2A, 2B, and 2C are diagrams of the operation of a linear peristaltic pump on a segment of compliant tubing showing in particular the establishment of a compliant fluid control segment.

Referring now to the drawings with more particularity, wherein like reference numerals designate like or corresponding elements among the several views, there is shown in FIG. 1 a system 10 for detecting occlusions in a fluid line upstream of a monitoring position. A fluid line 12, which may be an administration set formed of flexible tubing, is positioned between a fluid supply 14 and a patient 16 and comprises an upstream portion 18, a downstream portion 20, and a compliant pumping segment 22 (shown in FIGS. 2A, 2B and 2C) operated on by the pump 24. In this case, the fluid supply 14 comprises an inverted bottle. The compliant pumping segment 22 is operated on by a flow control device, which comprises in this embodiment an infusion pump 24, to form a compliant chamber as will be described in more detail below. A pressure sensor 26 is coupled to the downstream portion 20 to sense the downstream pressure and provide a signal representative of that sensed pressure. An analog-to-digital converter 28 is coupled to the pressure sensor 26 to provide a digital signal to a signal processor 30, shown in this case as a microprocessor, which is part of the pump assembly apparatus.

Figure 2B:
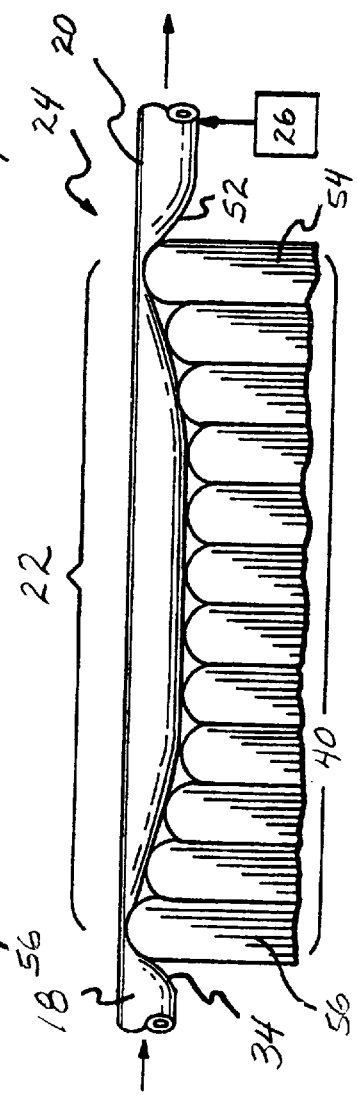
Figure 2C:
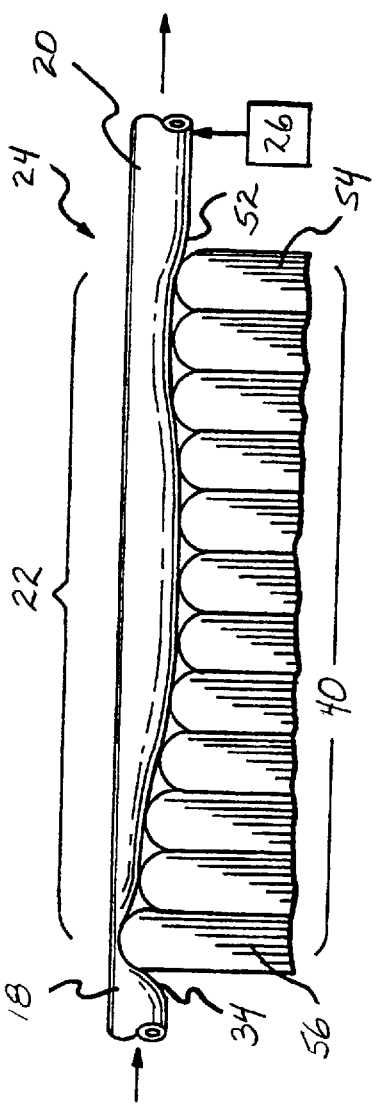

In the embodiment of FIG. 1, the upstream portion 18 has an upstream end 19 that is connected to the supply bottle 14 through a drip chamber 32. The upstream portion 18 supplies fluid to the infusion pump 24, which in the embodiment of FIGS. 2A, 2B, and 2C is a linear, finger-type peristaltic pump. The pressure of the fluid at the pump inlet 34 will be the upstream or "head" pressure. A motor 36 and control electronics 38 are used to drive the peristaltic fingers 40 of the linear peristaltic pump 24. The control electronics 38 and motor 36 are capable of temporary reversal of the infusion pump 24 for a selected number of degrees of rotation in a specific portion of the rotational cycle of the pump.

The pump system in this embodiment further comprises the microprocessor 30, a memory 42, an alarm 44, an operator control panel 46, and a display 48. The display unit 48, an option that may be desirable in various applications of the invention, may comprise a monitor or strip-chart recorder for displaying various parameters such as the downstream pressure, pressure difference, and average downstream pressure as determined by the microprocessor 30. Mounted at the downstream end 21 of the downstream portion 20 is a cannula 50 used to connect the downstream portion 20 to the vascular system of the patient 16. The pump 24 supplies the parenteral fluid to the patient 16 at a selected rate and pressure that may be different from the upstream pressure. In one embodiment, all of the items represented by boxes in FIG. 1 are located in a common housing.

In some prior systems, the output signal from the pressure sensor 26 is processed to detect the existence of a downstream occlusion, infiltration, or other condition. Some of these systems are mentioned in the preceding Background section. Thus, a pressure sensor 26 that can supply a downstream pressure signal is already installed in some pump systems.

Further associated with the microprocessor 30 and operator control panel 46 is an alarm 44 responsive to comparisons of pressure data with one or more reference threshold pressures in accordance with the discussion below.

A typical linear peristaltic pump operates by sequentially occluding a segment of flexible tubing by means of cam activated or cam driven occluding fingers. The pressure is applied to sequential adjacent locations of the tubing, beginning at the inlet end of the pump and working toward the outlet end. At least one finger is always pressing hard enough to occlude the tubing. As a practical matter, one finger does not retract from occluding the tubing until the next one has already occluded the tubing; thus, at no time is there a direct fluid path from the inlet to the outlet of the pump.

Referring now to FIGS. 2A and 2B, the operation of a linear peristaltic pump 24 in forming a pumping control segment 22 at head pressure is shown. The peristaltic pump 24 shown is a twelve-finger type, but other pump types may also be used with the invention, such as pumps utilizing peristaltic rollers or similar devices. The invention may also be used with piston-type pumps, such as that shown in U.S. Pat. No. 4,872,873 to Gorton et al.

The peristaltic pump fingers, indicated collectively by numeral 40, create a moving zone of occlusion throughout the length of a compliant pumping control segment 22. In FIG. 2A, the most downstream part of the compliant pumping segment or pump outlet 52 is occluded by the most downstream peristaltic finger 54 while the most upstream peristaltic finger 56 has not yet occluded the pumping control segment 22 at the pump inlet 34. Thus, fluid at upstream pressure is flowing into the pumping segment 22 from the upstream portion 18 but is prevented from communicating with the fluid in the downstream portion 20 by the occlusion caused by the most downstream peristaltic finger 54. Therefore, the pumping segment 22 is now at upstream or head pressure.

In FIG. 2B, formation of an isolated fluid pumping control segment 22 at upstream pressure is shown. As discussed above, the most upstream finger 56 occludes the fluid line 12 before the occluding downstream finger 54 retracts, thereby preventing a direct fluid flow between the fluid supply 14 and the patient 16. Thus, there exists a point in time when both fingers 54 and 56 occlude the fluid line as is shown in FIG. 2B, thereby forming the isolated fluid chamber which has trapped fluid at upstream pressure.

In FIG. 2C, the most upstream peristaltic finger 56 continues to occlude the pumping segment 22 as the most downstream finger 54 retracts from the occluding position. The fluid at upstream pressure, which had been isolated in the pumping segment 22, is now free to communicate with the fluid in the downstream portion 20. Thus, as shown in FIGS. 2A, 2B, and 2C, the pumping segment 22 is alternately in fluid communication with the upstream portion 18 and the downstream portion 20 of the fluid line.

When the most downstream peristaltic finger 54 retracts thereby allowing fluid communication between the downstream portion 20 and the pumping segment 22, the most upstream peristaltic finger 56 has already occluded the fluid line. Thus, a bolus of fluid at upstream pressure, the bolus being the quantity stored in the isolated chamber formed in FIG. 2B in the pumping segment 22, is released into the downstream portion 20 of the fluid line. Upon its release, the pressure in the pumping segment 22 and the pressure in the downstream portion 20 will equalize. A temporary pressure difference is produced that will be sensed by the downstream pressure sensor 26.

Because the fluid stored in the pumping control segment 22 is at upstream pressure, the pressure difference is proportional to the pressure differential between the upstream and downstream portions of the fluid line. In the case of an upstream occlusion, the pump will produce a large negative pressure, i.e., below atmospheric, very quickly. Thus, where an upstream occlusion is present, a negative pressure is created in the pumping segment 22 when the pumping segment 22 is in fluid communication with the upstream portion 18. The negative pressure may cause the walls of the pumping segment 22 to partially collapse. When the pumping segment 22 is subsequently placed in fluid communication with the downstream portion 20 of the fluid line 12, an aspiration of fluid occurs from the downstream portion 20 to the pumping segment 22 due to the partial vacuum in the pumping segment 22. This results in a large negative pressure difference at the pressure sensor 26 that is readily identifiable.

By itself, a large negative pressure difference is a strong indicator of an upstream occlusion. However, large pressure differences can occur in the absence of an upstream occlusion. For example, large pressure differences can also be generated by high downstream pressures. Accordingly, a large pressure difference is used in concert with other indicators to avoid false alarms.

Figure 3:
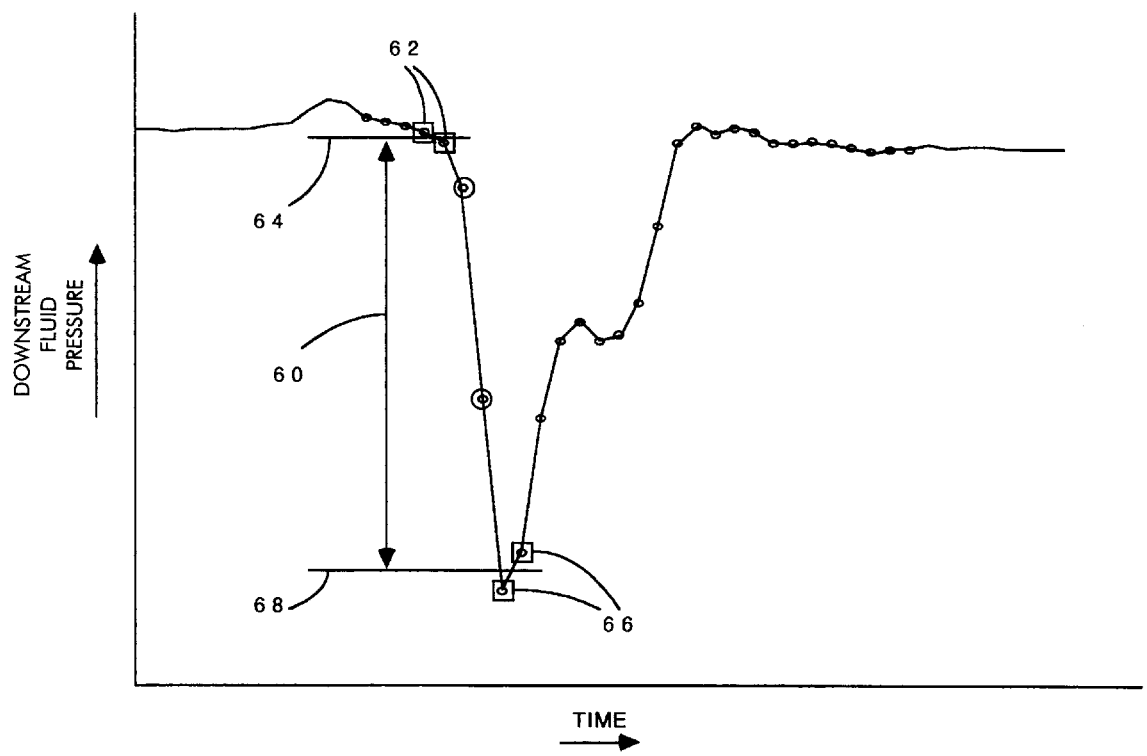
FIG. 3 is a diagram plotting downstream fluid pressure as a pumping control segment at head pressure is opened to fluid communication with a downstream end of a fluid line.

FIG. 3 shows a plot of downstream fluid pressure as the pumping control segment 22 containing fluid at upstream pressure is opened to fluid communication with the downstream portion. In a preferred embodiment, the pressure difference 60 is detected by a six-sample sliding difference algorithm that averages the two trailing samples 62 into a ledge value 64 and the two leading samples 66 into a bottom value 68 as shown in FIG. 3. The ledge value 64 corresponds to an estimate of the pressure just before the pumping segment is opened to fluid communication with the downstream portion, while the bottom value 68 corresponds to an estimate of the pressure just after the pumping segment opening. The pressure difference 60 is defined as the difference between the ledge value 64 and the bottom value 68. The algorithm window is parametrically specified in terms of motor step number (or similar parameter, depending on the particular pump mechanism) so that the sliding difference algorithm runs from just before to just after the pumping segment is opened to fluid communication with the downstream portion. For example, in a twelve-member peristaltic pump (such as a twelve-fingered linear peristaltic pump), the sliding difference algorithm starts before the cam 12:1 transition and ends after the 12:1 transition.

Although a particular algorithm has been described with respect to FIG. 3, that is merely one embodiment. Other methods of detecting the pressure difference may also be used, with the particular method depending on the particular application.

Monitoring the downstream pressure over time allows an average pressure downstream of the pump to be determined. In a preferred embodiment, the average pressure is a mean pressure determined over one entire pump motor revolution. The mean pressure $P_{ave}$ may be determined using various formulas, including:

$$P_{ave} = \frac{\int_0^{360} P(\theta)d\theta}{360}$$

for pumps having a 360 degree cycle, and $$P_{ave} = \frac{\sum_{\text{first step}}^{\text{last step}} P(n)}{\text{last step} - \text{first step} + 1}$$

for pumps having a stepped cycle. The average pressure is used to determine the existence of an upstream occlusion by comparison to a primary threshold pressure and, in a preferred embodiment, a secondary or cautionary threshold. Additionally, in another aspect, the average pressure is used to differentiate between a downstream occlusion and an upstream occlusion. An upstream occlusion will not be determined when the average pressure is increasing at a rate indicative of a downstream occlusion. Upstream occlusions are associated with decreasing average pressure or steady-state average pressure. In the case where the average pressure has a positive slope of more than a few mmHg, an upstream occlusion is not indicated and the system will not declare one.

Figure 4:
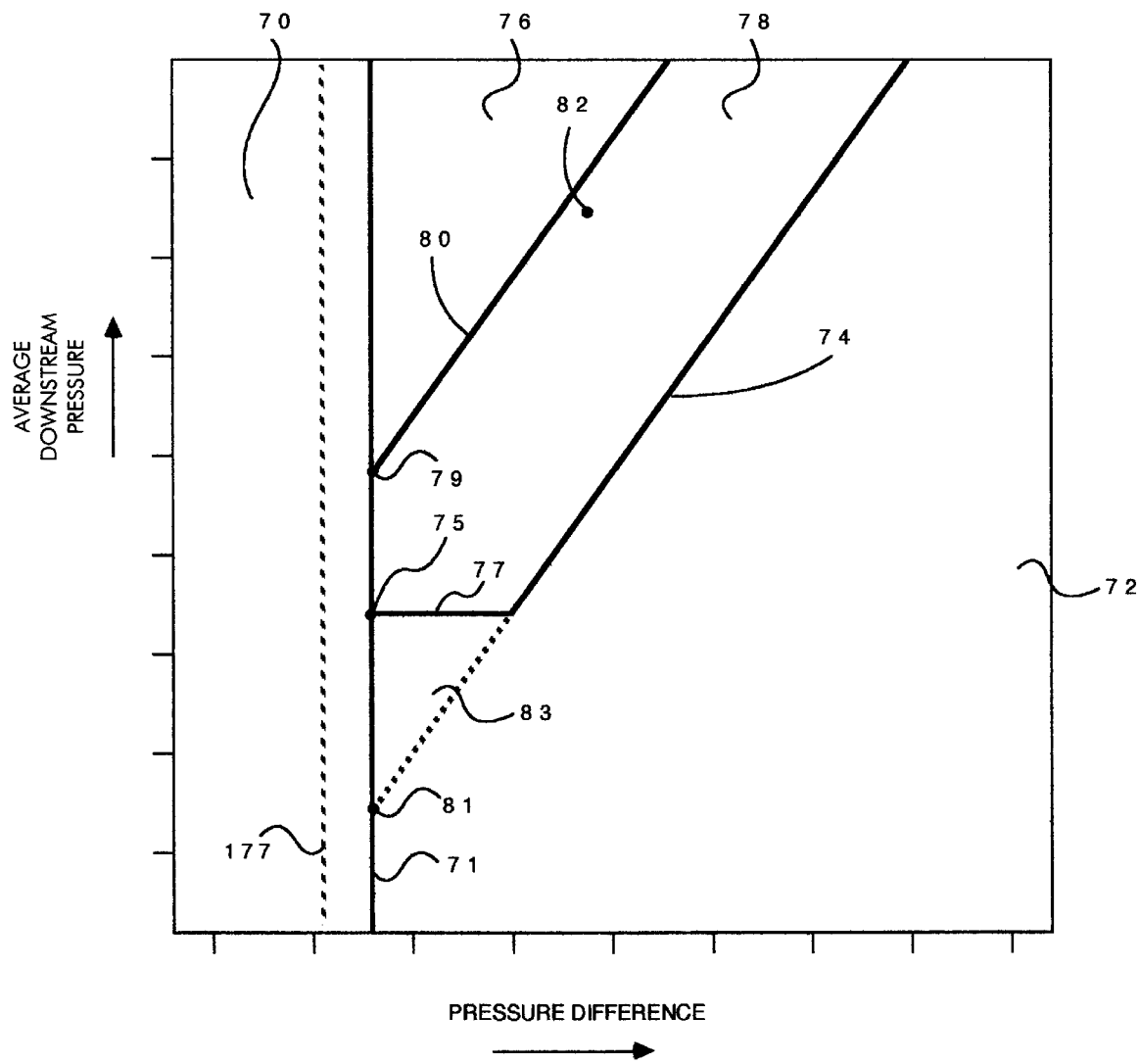
FIG. 4 is a diagram showing the relationship between average downstream pressure, pressure difference, a primary threshold pressure, and a cautionary threshold pressure.

FIG. 4 shows the relationship between the pressure difference, the pressure difference cutoff, the average pressure, and the primary, and cautionary threshold pressures. Four distinct regions are shown. The first region 70 corresponds to a situation where the pressure difference is so low that, regardless of the average pressure, no upstream occlusion is determined to exist. This region 70 includes pressure differences that are less than (i.e., to the left of) the pressure difference cutoff line 71. In one embodiment, the cutoff line was set within the range of 110 to 130 mmHg with a nominal setting at 125 mmHg.

The second region 72, also known as the determinate occlusion region, corresponds to situations where the pressure difference exceeds the pressure difference cutoff line 71 and the average pressure is less than the primary threshold pressure as indicated by the primary threshold line 74. When this combination of pressures exists, the system determines that an upstream occlusion exists.

The third region 76 corresponds to a situation where, although a relatively high pressure difference is detected, the average pressure is also relatively high and is above both the primary threshold pressure 74 and the secondary (i.e., cautionary) threshold 80. Thus, in the third region 76, no occlusion is determined to exist.

The fourth region 78, known as the possible upstream occlusion or cautionary region, corresponds to a situation where the pressure difference is above (i.e., to the right of) the pressure difference cutoff line 71 and the average pressure is above the primary threshold 74 but below the secondary or cautionary threshold 80. Where the pressure difference and average pressure map into this third or possible USO region 78 for one or more revolutions of the pump cycle, the system activates a pump reversal confirmation test to validate the presence or absence of an upstream occlusion. The pump reversal test is discussed in greater detail below with respect to FIG. 7.

The fourth region 78 is defined on two sides by the cautionary threshold line 80 and the primary threshold line 74, which correspond to cautionary threshold values and primary threshold values respectively, and on a third side by the pressure difference cutoff line 71. In the present embodiment, the primary threshold line 74 will not vary during operation of the system. However, the cautionary threshold pressure line 80 is adaptable and may be adjusted during operation of the system to prevent unnecessary pump reversal confirmation tests or to enhance system sensitivity.

In one embodiment, the primary threshold is determined in accordance with:

*Primary Threshold=(1/K)×(Press. Diff−Press. Diff. Cutoff)+InterceptP* where:

$$K = \frac{C_{fluid\ tube}}{C_{fluid\ tube} + C_{downstream}}$$

$C_{fluid\ tube}$=compliance in $\mu$L/mmHg of the pumping segment from intake to most downstream finger $C_{downstream}$=compliance in $\mu$L/mmHg of the downstream fluid tube to the patient InterceptP=the intercept point 81 of the primary threshold line 74 with the pressure difference cutoff line 71 (FIG. 4) if the primary threshold line consisted of a straight line (as shown in dashed lines). In one embodiment, InterceptP corresponds to 0 mmHg.

In one embodiment, K ranged from 0.320 to 0.350 with a nominal value of 0.333.

The primary threshold line shown in FIG. 4 comprises a horizontal portion 77 bent at an angle to the main portion 74. As shown in FIG. 4, if the primary threshold line 74 were to remain straight, it would intersect the pressure difference cutoff line 71 at point 81. A triangle 83 is formed between the dashed line portion of the threshold line 74, the bent portion 77 and the cutoff line 71. Because in one embodiment the pressure sensor was found to have an offset of the amount indicated by the point 75 (75 mmHg), the bent portion 77 was used to add the triangle 83 to the first region 72 so that pressure combinations in this triangular area 83 would be determined to be USOs.

In one embodiment, the cautionary threshold line 80 is determined in accordance with:

*Caut. Threshold=1/K(Press. Diff−Press. Diff Cutoff)+InterceptB* where: InterceptB =intercept point 79 of the cautionary threshold line with the pressure difference cutoff line 71. In one embodiment, InterceptB could range from a minimum point of 0 mmHg to a maximum point of 300 mmHg with the minimum point of InterceptB corresponding to InterceptP.

Where a particular pressure difference and average pressure combination, such as the combination indicated by point 82, maps into the fourth or cautionary region 78 and a pump reversal confirmation test (described below) is initiated that determines no upstream occlusion exists, the cautionary pressure threshold line 80 can be adjusted (adapted) in the negative direction as described below. The amount of adjustment is determined by empirical data, and varies depending on the particular apparatus and circumstances. In one embodiment, the adjustment factor was equal to approximately 25 mmHg. In any case, no adjustment is permitted that would lower the cautionary threshold to a point below the primary threshold.

Figure 4A:
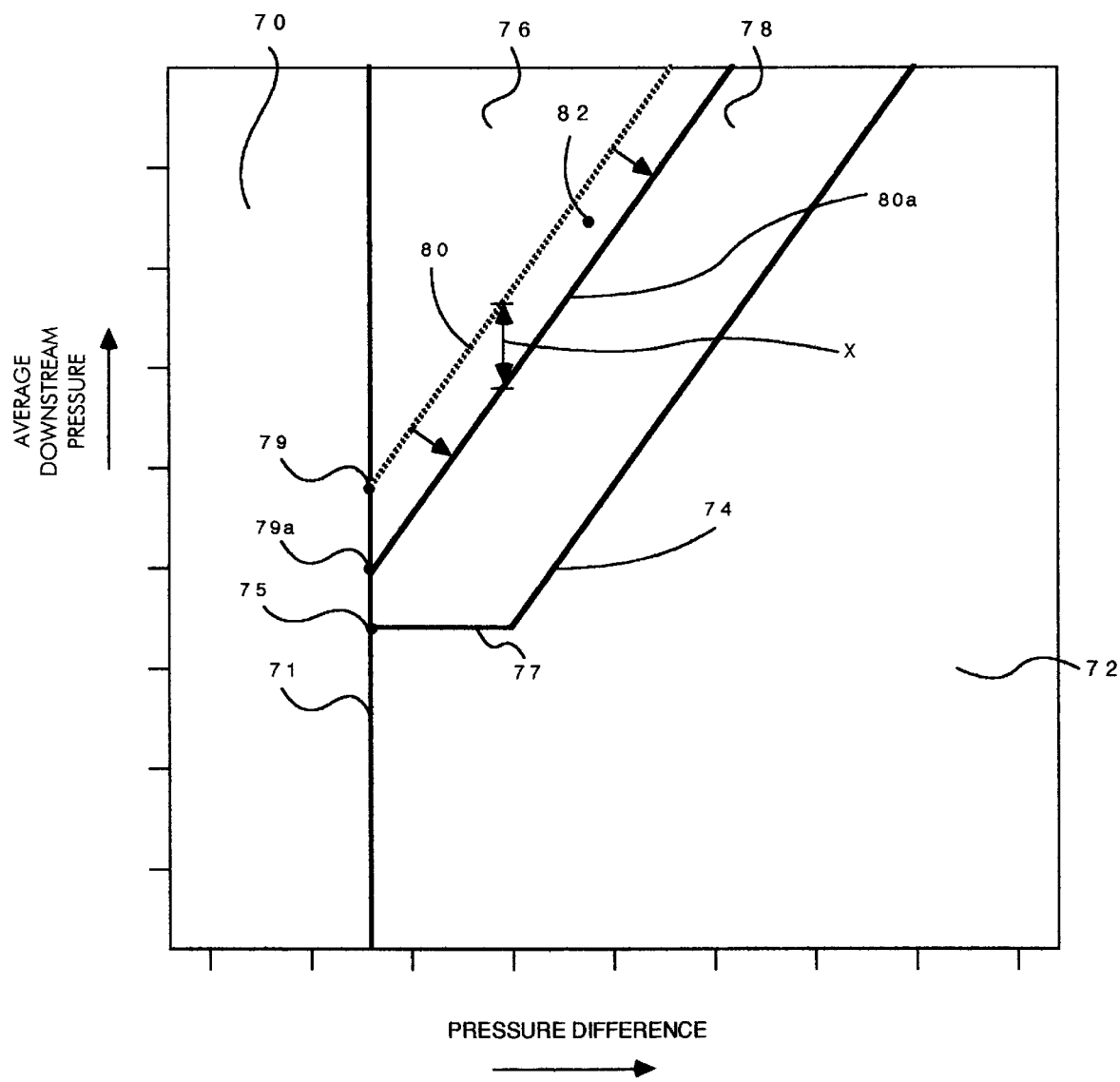
FIG. 4A is a diagram showing a modified relationship between a pressure difference, an average downstream pressure, a primary threshold pressure, and a negatively adjusted cautionary threshold pressure.

FIG. 4A shows a resulting negatively adjusted cautionary threshold pressure line 80*a* and new InterceptB 79*a* that reduces the cautionary region 80 so that it no longer incorporates the pressure difference and average pressure combination indicated by point 82 thus lowering sensitivity.

*New InterceptB (lower)=InterceptB (previous)–(Prev. Caut. Thresh.–Press. Ave.)–Δ* where: Δ=a fixed pressure, in one embodiment ranging from 40–100 mmHg and nominally selected to be 75 mmHg.

Figure 4B:
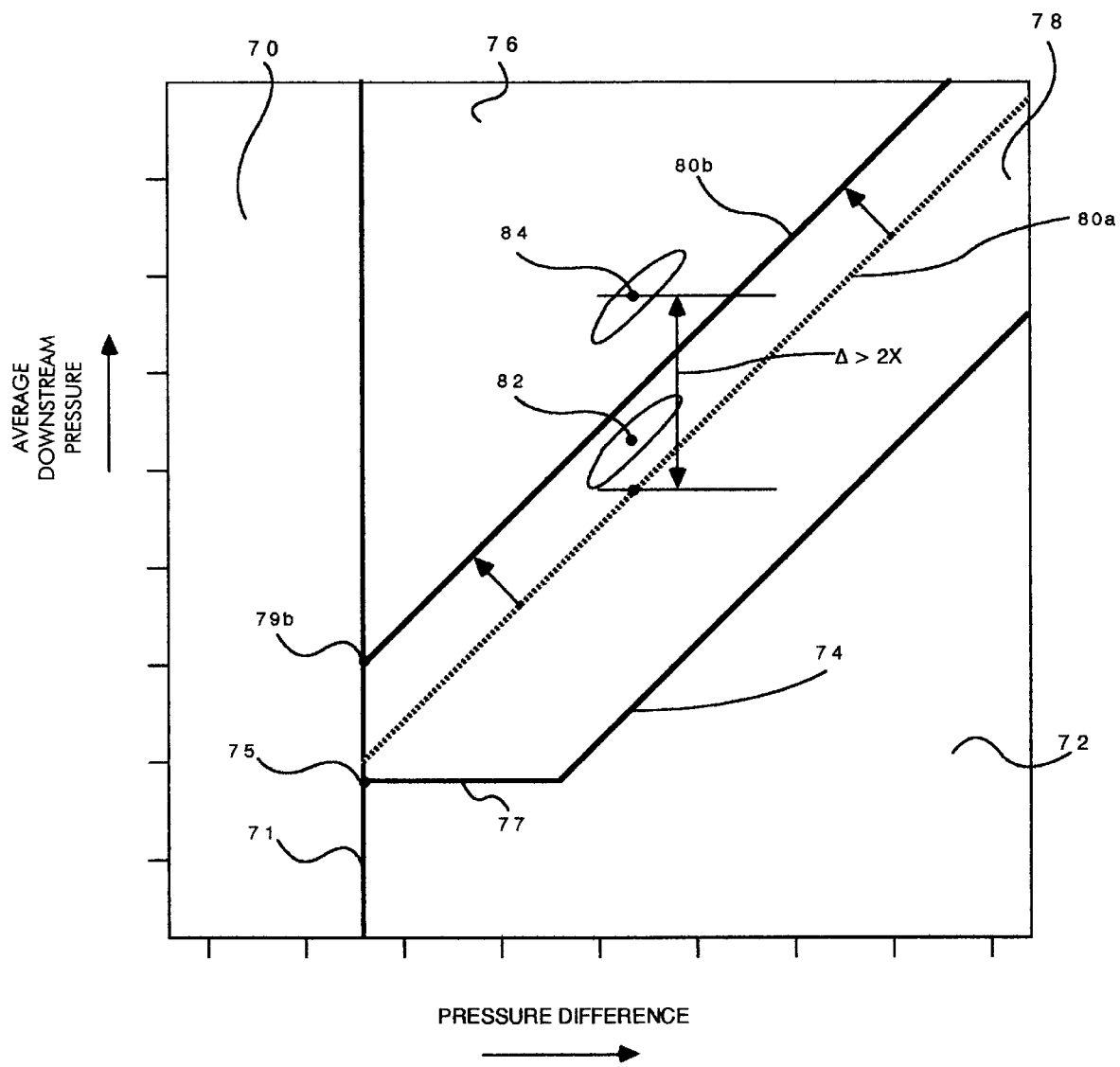
FIG. 4B is a diagram showing a modified relationship between a pressure difference, an average downstream pressure, a primary threshold pressure, and a positively adjusted cautionary threshold pressure.

The cautionary threshold pressure line 80 can also be positively adjusted to enlarge the cautionary region 78 and hence enhance the sensitivity of the system. Such an adjustment may be made when, as an example, the cautionary threshold pressure line 80*a* has previously been negatively adjusted to accommodate previous pressure difference/average pressure combinations, but recent pressure difference/average pressure combinations are mapping well beyond the negatively adjusted cautionary threshold line 80*a* and the previous unadjusted line 80. For example, in the embodiment shown in FIG. 4B, the negatively adjusted cautionary threshold line 80*a* was negatively adjusted by an amount x, but recent operating conditions map into an area around point 84 that is above the negatively adjusted cautionary threshold line 80*a* by a factor of greater than 2*x. Under such circumstances, a positive adjustment may be made to create a positively adjusted cautionary threshold line 80*b*.

The positive adjustment, in one embodiment, is in an amount equal to one half of the difference between the negatively adjusted cautionary threshold line 80*a* and the recent pressure difference/average pressure combination 84. Thus, a positively adjusted cautionary threshold line 80*b*, with a positively adjusted InterceptB 79*b*, increases the cautionary region 78 while still excluding recent operating conditions.

*New InterceptB (higher)=Press. Ave.–Δ–1/K(Press. Diff–Press. Diff. Cutoff)*

In one embodiment, the cautionary threshold line can only be moved in the positive direction if it has previously been lowered as a result of a pump reversal test and that pump reversal test occurred more than four pump revolutions ago. Additionally, it cannot be moved to a position above the maximum average pressure (the maximum for InterceptB)

In a preferred embodiment, the system performs a comparison of average pressure to threshold pressures once per revolution of the peristaltic pump. In a further embodiment, the system requires an average pressure to be below the primary threshold pressure for a predetermined number, such as three, of successive pump revolutions before an upstream occlusion alarm is generated.

In a preferred embodiment, the thresholds are calculated based on each pressure difference. In another embodiment, threshold pressures are selected from a list or table of threshold pressures stored in memory 42 (FIG. 1).

Figure 5:
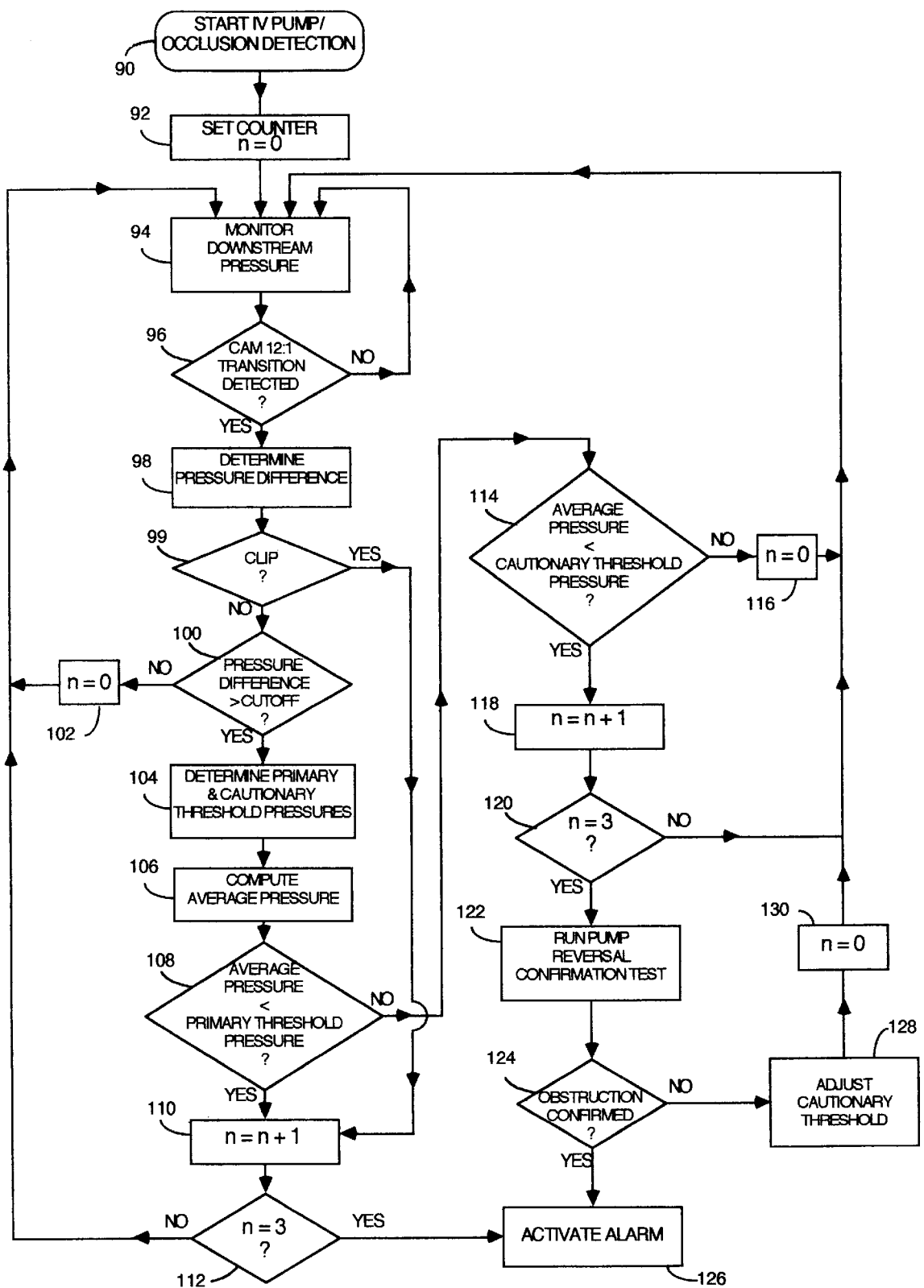
FIG. 5 is a flow diagram showing the upstream occlusion logic test performed in another embodiment of the invention.

FIG. 5 is a flow diagram showing the upstream occlusion analysis performed in one embodiment of the invention. In the embodiment of FIG. 5, upon activation of the occlusion detection system (step 90), a counter n is initially set to a zero value (step 92). The system monitors downstream fluid pressure via frequent or continuous pressure signals from a pressure sensor (step 94).

When the pump opens the pumping control segment to communication with the downstream portion of the fluid line, which in the embodiment shown is when the cam 12:1 transition is detected (step 96), the system determines the resulting pressure difference (step 98). The pressure difference signal is analyzed for the presence of clipping (step 99).

Figure 6:
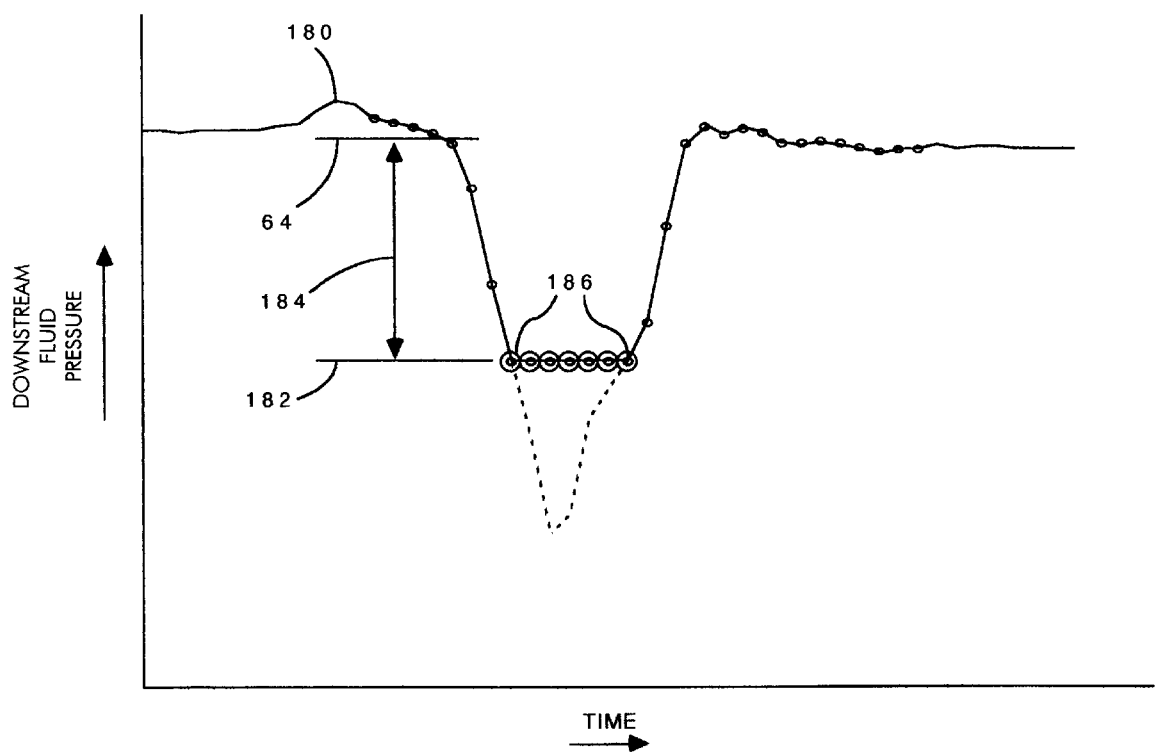
FIG. 6 presents a downstream fluid pressure waveform subjected to clipping.

In FIG. 6, the pressure waveform 180 provided by the pressure sensor had begun to indicate a pressure difference but then it was truncated 182 or "clipped." However, highly damped conditions downstream can also result in waveforms that appear to be flattened and resemble the clipped waveform shown in FIG. 6. Thus, the system analyzes the pressure data further before a clipped waveform is considered to exist. In one embodiment, the average pressure must be less than zero and a pressure difference of at least 50 mmHg must exist before the system considers that a waveform can be a candidate for clipping. That is, a pressure difference of at least 50 mmHg negative 184 from the ledge value 64 must first exist. Once it has been determined that a pressure difference signal is being provided, the processor monitors successive samples of the pressure signal. If the sum of the differences between a select number of sequential samples, such as the seven samples 186 in FIG. 6, should be under a predetermined threshold, the processor determines that clipping is occurring. The actual pressure in the fluid line is shown in FIG. 6 by dashed lines.

In one analysis, clipping is determined to exist when the following condition is met:

$$\sum_{n=1}^{6} |(P_n - P_{n-1})| < \text{Clip Threshold}$$

where: n=the number of the particular sample, with seven samples numbered 0 through 6

$P_n$=the pressure sensed

The Clip Threshold in one embodiment was selected to be 3 mmHg.

Referring now once again to FIG. 5, if clipping is found, the count of n is increased by one (step 110). As can be seen, if the processor finds a clipped signal in three successive pressure difference signals (step 112), the alarm is activated (step 126).

The system also compares the pressure difference to the pressure difference cutoff 71 (step 100) and if the difference is below the cutoff, the number n is reset to zero (step 102) regardless of the average pressure. However, if the pressure difference exceeds the cutoff 71, the system determines the corresponding primary and cautionary threshold pressures (step 104). The system also calculates the average fluid pressure (step 106), preferably for the pump cycle that has just ended with the 12:1 cam transition. Depending on the particular embodiment, the average fluid pressure may be continuously calculated and updated. The system compares the average pressure to the primary pressure threshold (step 108).

If the average pressure is lower than the primary threshold pressure, an occlusion is indicated and the system will increase the number n by one (step 110), determine if n is equal to three (step 112) and if it is not, the occlusion alarm is not activated, and the system monitors subsequent pump cycles until three sequential cycles show the average pressure to be below the primary threshold pressure. If n is equal to three, an alarm is provided (step 126).

If the average pressure is greater than the corresponding primary threshold pressure, the system in the embodiment shown compares the average pressure to the cautionary threshold (step 114). If the average pressure is not less than the cautionary threshold, the system resets the number n to zero (step 116) and repeats the monitoring process. However, if the average pressure is lower than the cautionary threshold, the system adds one to the number n (step 118) and determines if n is equal to three (step 120). If not equal to three, the system repeats the monitoring process by returning to step 94. If equal to three, the system runs the pump reversal confirmation test 122. The test is monitored for confirmation of an upstream occlusion (step 124) and if one is confirmed, an alarm is given (step 126). If no upstream occlusion is confirmed, the cautionary threshold is adjusted (step 128) and the monitoring process repeated at step 94 after resetting the number n to zero (step 130).

In the embodiment discussed above with respect to FIG. 5, the pressure difference is used to determine an average pressure threshold, with the average pressure then compared to the threshold to detect USOs. However, since pressure difference and average pressure are parametrically related, the system could also detect USOs if the logic were reversed, i.e., if the average pressure were used to determine a pressure difference threshold, and the pressure difference then compared to the threshold to detect USOs. More specifically, the average pressure could be used to determine a primary (i.e., determinative) pressure difference threshold and a secondary or cautionary pressure difference threshold. If the pressure difference is greater than the primary pressure difference threshold, a USO is indicated. If the pressure difference is less than the primary pressure difference but greater than the cautionary pressure difference, a possible USO is indicated. If the pressure difference is less than both the primary and cautionary pressure thresholds, no USO is indicated.

Figure 7:
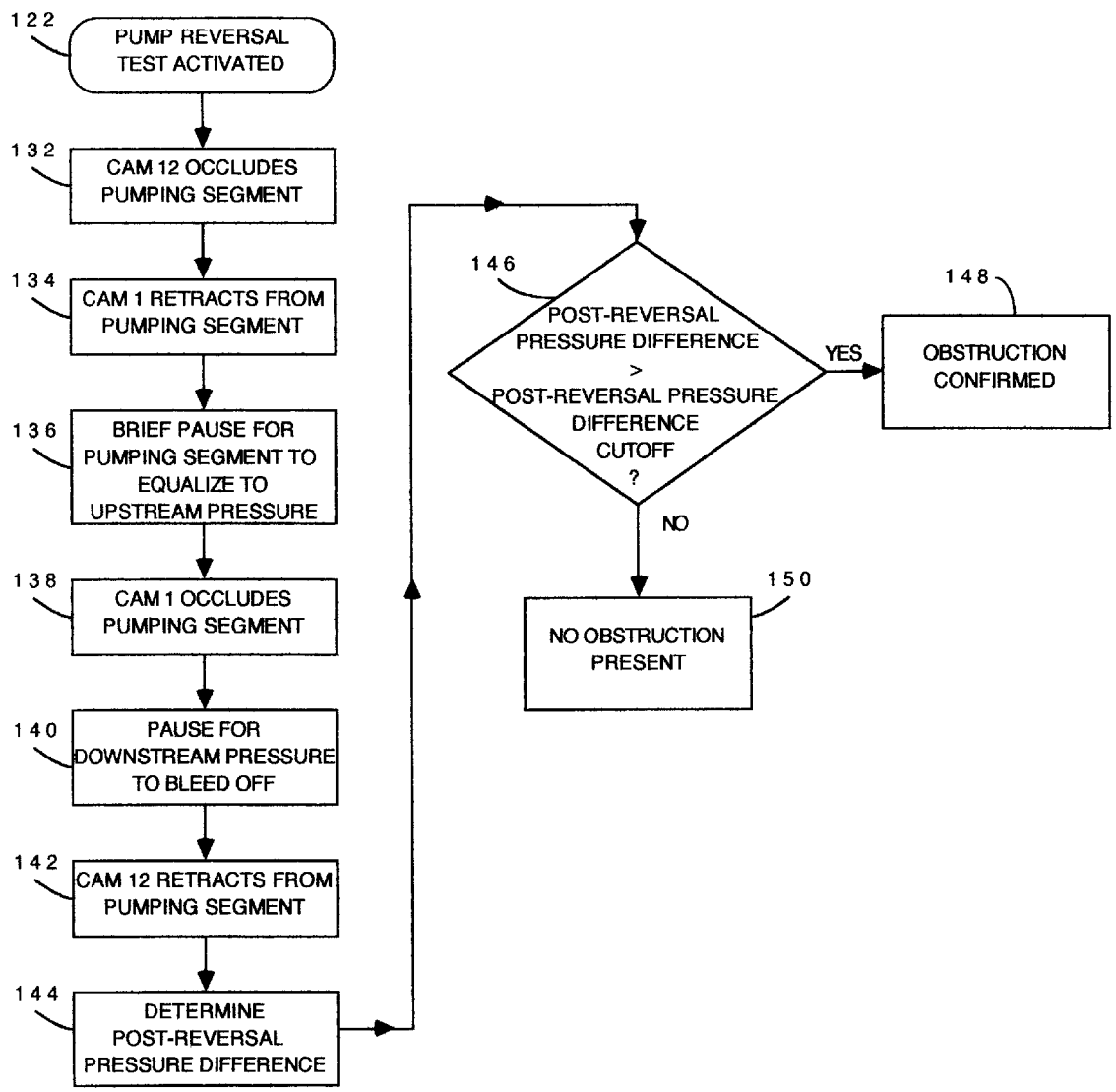
FIG. 7 is a flow diagram showing the pump reversal confirmation test performed in one embodiment of the invention.

FIG. 7 is a flow diagram showing a pump reversal confirmation test of the type referred to in step 122 of FIG. 5. The steps shown in the embodiment of FIG. 7 are specific to a twelve-finger cam-driven pump mechanism, but the general approach involved is applicable to a variety of pump mechanisms.

If in the embodiment shown in FIG. 5, the system detects a possible USO in three sequential pump revolutions, the system initiates a pump reversal confirmation test (step 122) wherein a post-reversal pressure difference is generated by reversing the pump motor, causing finger twelve to occlude the pumping segment and isolate the pumping segment from downstream pressure (step 132). Next, the most upstream finger retracts from the pumping segment (step 134), thereby exposing the pumping control segment to upstream pressure. Motor operation is briefly stopped to allow the pumping segment to equalize to upstream pressure (step 136). The pump motor returns to forward operation, whereby the most upstream finger occludes the pumping segment and isolates the pumping control segment 22 (FIG. 2B) from the upstream pressure (step 138) so that it contains fluid at upstream pressure. After a brief delay (step 140), the most downstream finger retracts from the pumping segment (step 142) thereby opening the pumping control segment to fluid communication with the downstream portion. The delay (step 140), which in one embodiment lasts approximately ten seconds, allows the downstream pressure to bleed off. This delay is important where a large pressure difference is the result of a build-up of downstream pressure due to a high downstream resistance. The delay allows the downstream pressure to dissipate as fluid flows through the resistance, thereby reducing the post-reversal pressure difference.

The post-reversal pressure difference is determined (step 144) as the pumping control segment is placed in fluid communication with the downstream portion of the fluid line, which occurs when the most downstream occluding finger, which in this embodiment is finger twelve, retracts from the pumping segment. The post-reversal pressure difference is compared with a post-reversal pressure difference cutoff (step 146) to determine the presence (step 148) or absence (step 150) of an obstruction.

Since a complete post-reversal cycle of the pump has not occurred at the time that the post-reversal pressure difference is determined, insufficient data is available to determine a post-reversal pressure average for a complete pump cycle. Accordingly, the confirmation test relies solely on comparing the post-reversal pressure difference to a post reversal pressure difference cutoff. The post-reversal pressure difference cutoff is preferably set to be less than the pressure difference cutoff 71. In one embodiment shown in FIG. 4, the post-reversal pressure cutoff 177 was set within the range of 80–100 mmHg and set nominally at 100 mmHg, corresponding to approximately 80% of the pressure difference cutoff 71.

If the post-reversal pressure difference is below the post-reversal pressure difference cutoff 177, the system determines that no upstream occlusion exists and adapts the cautionary threshold pressure accordingly. If the post-reversal pressure difference is above the post-reversal pressure difference cutoff 177, the system determines that an upstream occlusion exists that was previously masked by a high downstream pressure.

The pump reversal confirmation test is defined by the following sequence of events:

1. Pump reversal test is activated when, during "n" sequential pump revolutions, the average pressure is less than the cautionary threshold pressure but is above the primary threshold pressure (i.e., the pressure difference/average pressure combination maps into the cautionary region shown in FIG. 4);
2. The system computes the desired end position of the pump's reverse travel, which corresponds to the point where the pumping control segment is opened to the upstream portion but closed to the downstream portion;
3. Pump cycle is reversed to the desired end position;
4. Pump operation is stopped at the desired end position for a desired period of time to allow downstream pressure to bleed off;
5. Forward pump operation is resumed;
6. The post-reversal downstream pressure difference, occurring as the pumping control segment is opened to the downstream portion, is determined;
7. If the post-reversal pressure difference exceeds the post-reversal pressure difference cutoff, an occlusion is deemed to exist and an alarm signal is activated;
8. If the post-reversal pressure difference is less than the post-reversal pressure difference cutoff, no occlusion is deemed to exist and pump operation continues. The value of the cautionary threshold pressure may be adjusted downward, as discussed above with respect to FIG. 4A, to avoid further unnecessary pump reversal confirmation tests.

Although various specific embodiments have been disclosed, other embodiments may be used without departing from the spirit and scope of the invention. For example, other types of pumps may be used if the pump accommodates a compliant chamber capable of storing fluid at one of the pressures and subsequently connecting the chamber to the portion of the fluid line at the other pressure.

In view of the foregoing, it can be appreciated that the present invention provides a simple, low cost apparatus and method for detecting upstream occlusions in the fluid line in an IV fluid administration system without the necessity of modifying existing peristaltic pump mechanisms. In IV systems where a downstream pressure sensor has already been installed, the signal processing can be modified in accordance with the invention to provide such upstream condition detection. Placed in a downstream configuration, the system of the invention can be readily adapted to detect upstream occlusions in existing peristaltic pump IV infusion systems.

Although preferred and alternative embodiments of the invention have been described and illustrated, the invention is susceptible to modifications and adaptations within the ability of those skilled in the art and without the exercise of inventive faculty. Thus, it should be understood that various changes in form, detail and usage of the present invention may be made without departing from the spirit and scope of the invention.

What is claimed is:

1. A method for detecting the condition of a fluid delivery system that includes a fluid line having an upstream end coupled to a fluid supply and a downstream end coupled to a fluid receiver, the delivery system having a flow control means for operating on a fluid chamber to control the flow of the fluid in the fluid line, the method comprising the steps of:

(a) controlling fluid flow through the fluid line at a pumping segment between the upstream and downstream ends;

(b) alternately exposing the pumping segment to fluid pressure at the upstream end of the fluid line and to fluid pressure at the downstream end of the fluid line;

(c) sensing the pressure downstream of the pumping segment and providing a pressure signal;

(d) determining a value corresponding to an average downstream pressure;

(e) comparing said average pressure value to a primary threshold value; and (f) activating an occlusion alarm in response to the average pressure value being less than said primary threshold value.

2. A method for detecting the condition of a fluid delivery system that includes a fluid line having an upstream end coupled to a fluid supply and a downstream end coupled to a fluid receiver, the delivery system having a flow control means for operating on a fluid chamber to control the flow of the fluid in the fluid line, the method comprising the steps of:

(a) controlling fluid flow through the fluid line at a pumping segment between the upstream and downstream ends;

(b) alternately exposing the pumping segment to fluid pressure at the upstream end of the fluid line and to fluid pressure at the downstream end of the fluid line;

(c) sensing the pressure downstream of the pumping segment and providing a pressure signal;

(d) determining a value corresponding to an average downstream pressure;

(e) comparing said average pressure value to a primary threshold value;

(f) comparing said average pressure value to a cautionary threshold value, said cautionary threshold value being greater than said primary threshold value; and (g) activating a cautionary occlusion alarm in response to the average pressure value being less than said cautionary threshold value and greater than said primary threshold value.

3. The method of claim 2 including the further step of:

(h) activating a predetermined occlusion confirmation test in response to a cautionary occlusion alarm.

4. The method of claim 2 including, prior to step (e), the further steps of:

(i) determining a downstream pressure difference; and (j) deriving said primary threshold value and said cautionary threshold value as a function of the downstream pressure difference.

5. A method for detecting the condition of a fluid delivery system that includes a fluid line having an upstream end coupled to a fluid supply and a downstream end coupled to a fluid receiver, the delivery system having a flow control means for operating on a fluid chamber to control the flow of the fluid in the fluid line, the method comprising the steps of:

(a) controlling fluid flow through the fluid line at a pumping segment between the upstream and downstream ends;

(b) alternately exposing the pumping segment to fluid pressure at the upstream end of the fluid line and to fluid pressure at the downstream end of the fluid line;

(c) sensing the pressure downstream of the pumping segment and providing a pressure signal;

(d) determining a value corresponding to an average downstream pressure;

(e) determining a downstream pressure difference;

(f) deriving a primary threshold value as a function of the downstream pressure difference; and (g) comparing said average pressure value to the primary threshold value.

6. A method for detecting the condition of a fluid delivery system that includes a fluid line having an upstream end coupled to a fluid supply and a downstream end coupled to a fluid receiver, the delivery system having a flow control means for operating on the fluid chamber to control the flow of the fluid in the fluid line, the fluid upstream of the flow control means being at head pressure, the method comprising the steps of:

(a) controlling fluid flow through the fluid line at a pumping segment between the upstream and downstream ends;

(b) alternately exposing the pumping segment to fluid pressure at the upstream end of the fluid line and to fluid pressure at the downstream end of the fluid line;

(c) sensing the pressure downstream of the pumping segment and providing a pressure signal;

(d) monitoring the pressure signal and determining the downstream pressure difference between the pumping segment exposed to the downstream pressure and exposed to the upstream pressure;

(e) determining a primary threshold pressure as a function of said downstream pressure difference;

(f) monitoring and determining an average downstream pressure;

(g) comparing the average pressure to said primary threshold pressure; and (h) generating an upstream occlusion signal in response to said average pressure being less than said primary threshold pressure.

7. The method of claim 6 further comprising the steps of:

(i) determining a cautionary threshold pressure as a function of said pressure difference;

(j) comparing the downstream pressure difference to said cautionary threshold pressure; and (k) generating a potential occlusion signal in response to said average pressure being less than said cautionary threshold pressure.

8. The method of claim 7 wherein in response to a potential occlusion signal the method further comprises the steps of:

(l) reversing operation of said flow control means to open the upstream end of the pumping segment;

(m) resuming forward operation of said flow control means to open the downstream end of the pumping segment;

(n) determining a post-reversal downstream pressure difference occurring downstream end of the pumping segment is opened;

(o) comparing said post-reversal pressure difference to a post-reversal cut-off pressure; and (p) generating an upstream occlusion signal if said post-reversal pressure difference exceeds said post-reversal cut-off pressure.

9. The method of claim 8 further comprising the steps of:

(q) adjusting the cautionary threshold if said post reversal pressure difference is less than said post-reversal cut-off pressure.

10. The method of claim 8 further comprising the step of:

(r) adjusting the cautionary threshold if said post-reversal pressure difference exceeds said post-reversal cut-off pressure.

11. The method of claim 6 further comprising the step of:

(s) comparing the pressure difference to a primary cut-off pressure.

12. The method of claim 10 wherein step (s) is performed prior to step (e), and steps (g) and (h) are performed in response to the pressure difference exceeding said primary cutoff pressure.

* * * * *